United States Patent [19]

Horsley et al.

[11] Patent Number: 5,027,076

[45] Date of Patent: Jun. 25, 1991

[54] OPEN CAGE DENSITY SENSOR

[75] Inventors: William J. Horsley; Virgil R. Tucker, both of Boulder, Colo.

[73] Assignee: Ball Corporation, Muncie, Ind.

[21] Appl. No.: 471,577

[22] Filed: Jan. 29, 1990

[51] Int. Cl.[5] ........................ G01R 27/26; G01N 9/00

[52] U.S. Cl. .................................... 324/674; 324/690; 73/32 R

[58] Field of Search ............... 324/663, 674, 686, 690, 324/444, 443, 442, 450; 73/32 R, 437

[56] References Cited

U.S. PATENT DOCUMENTS

| | | | |
|---|---|---|---|
| 3,421,077 | 1/1969 | Liu et al. | 324/690 |
| 3,437,924 | 4/1969 | Tocanne | 324/690 |
| 4,177,669 | 12/1979 | Wenger | 73/32 A |
| 4,284,951 | 8/1981 | Dahl et al. | 324/444 |
| 4,543,823 | 10/1985 | Nagy et al. | 324/643 |
| 4,555,661 | 11/1985 | Benson et al. | 324/608 |
| 4,835,456 | 5/1989 | Lin et al. | 324/674 |

*Primary Examiner*—Reinhard J. Eisenzopf

*Assistant Examiner*—Maura K. Regan

*Attorney, Agent, or Firm*—Gilbert E. Alberding

[57] ABSTRACT

A light-weight density sensor has a rigid open structure that does not impede fluid flow and provides the ability to accurately and reproducably measure dielectric constant and densities over long distances without interference from connecting coaxial cables during periods of vibration and thermal shock. A novel immersion cell and an oscillator circuit provide a variable frequency output related to the dielectric constant of the cryogen within the immersion cell and from which the density of the cryogen can be determined. The immersion cell comprises an elongated electrode located centrally within an open outer electrode formed by a plurality of elongated conductors spaced around and from the central electrode conductor. The open outer electrode does not impede the flow of cryogen into the immersion cell and by its structure permits accurate density determinations dependent upon the dielectric constant of cryogen present within the cell.

19 Claims, 2 Drawing Sheets 10 14 14 17 13 11 15 14 15 14 12 L 2 2 14 13 14 16

OPEN CAGE DENSITY SENSOR

FIELD OF THE INVENTION

This invention relates to a system for determining the density of cryogenic liquids, solids, gases and mixtures and, more particularly, relates to an immersion cell for use in such systems.

BACKGROUND ART

The determination of density of cryogens, such as liquified gases and associated solids, gases and mixtures thereof, is a difficult problem because cryogens are volatile and measurements must take place at cryogenic temperatures.

U.S. Pat. No. 3,933,030 discloses a system of taking continuous simultaneous, or sequential, readings of density in a cryogenic tank to monitor density changes and thereby create a density profile of the content of the tank to avoid the occurrence of rollover, or density inversions which, when left unchecked, can create a sudden emission of large quantities of highly flammable and explosive gases. U.S. Pat. No. 3,933,030 suggests that the density of cryogenic liquids can be continuously determined electrically by the use of differential capacitance measurements. Density is determined from the Clausious-Mosotti equation by determining the dielectric constant of the cryogenic liquid with a dielectric cell of known capacitance, measuring the temperature of the cryogenic liquid and calculating the density of the cryogenic liquid from the Clausious-Mosotti equation.

Many systems have been disclosed for determining the dielectric constants of fluid materials. For example, U.S. Pat. No. 4,555,661 discloses method and apparatus for determining a dielectric constant of fluid materials through a differential capacitance technique. The disclosed apparatus of U.S. Pat. No. 4,555,661 consists of a three electrode device which may be placed in a container of fluid material. The electrodes of the device may be three planar electrodes or three coaxial cylindrical electrodes. The two remote electrodes are connected across the terminals of a free-running oscillator and determine its frequency of oscillation by their area and their separation and the dielectric constant of the material between the electrodes. The intermediate electrode is connected to a switch which alternatively connects the intermediate electrode to one of the remote electrodes and disconnects the intermediate electrode from the circuit thereby changing the frequency of oscillation. Dielectric constant is determined from the frequency difference.

U.S. Pat. No. 3,903,478 discloses a fluid density measuring device including fluid capacitance test cell comprising three coaxial conductive cylindrical electrodes surrounded by a protective outer tube. The test cell capacitor is formed by inner and outer concentric cylinders, which are interconnected, and the intermediate concentric cylinder and is connected with a 16 kHz precision oscillator to provide a current through the test cell capacitor that is proportional to the density of the fluid passing through the test cell. The 16 kHz precision oscillator also provides a current through another capacitor which is 180° out-of-phase, and both currents are directed to an amplifier which provides an output proportional to the difference in the currents and therefore the density of the fluid through the test cell.

U.S. Pat. No. 4,544,880 discloses a microwave probe for measuring the amount of contaminants or water in crankcase oil, comprising a coaxial cable having a tip including five substantially parallel wires shorted together at one end and connected at the other end to the coaxial cable. The microwave probe includes a central wire connected to the center wire of the coaxial cable and four outer wires connected to the sheath of the coaxial cable at one end and connected to each other and to the center wire at the other end. The size and geometry of the wires is selected so that the impedance of the tip, when immersed in oil, substantially matches the impedance of the coaxial cable. The dielectric constant of the oil and the contaminant content of the oil is measured by connecting the microwave probe to a microwave oscillator and measuring either the voltage level of the standing wave at a fixed position along the interconnecting coaxial cable, or the null location of the standing wave along the interconnecting coaxial cable, or the operating frequency of the microwave oscillator required to keep the standing wave in a fixed position along the interconnecting coaxial cable.

Other systems which have been disclosed for the measurement of dielectric constants of fluids include those disclosed in U.S. Pat. Nos. 3,375,716; 3,739,266; 4,011,746; 4,417,472; 4,429,272; 4,468,611; 4,673,869; and 4,751,476.

U.S. Pat. No. 3,375,716 discloses a multivibrator driven with a fluid cell capacitor as a sensor element in the timing circuit of the multivibrator, to provide a liquid level gauge by varying the frequency of the multivibrator as a result of variations in capacitance of the sensor as liquid fills the fluid cell capacitor.

U.S. Pat. No. 3,739,266 discloses a system for protecting the moisture content of material such as cottonseed by the variation in the dielectric constant of a flow of such material past capacitor plates. The capacitor plates of U.S. Pat. No. 3,739,266 are connected to an oscillator generating an electrical signal whose frequency is proportional to the dielectric constant of the material.

U.S. Pat. No. 4,011,746 discloses a liquid density measurement system comprising a capacitance probe and a temperature sensor both immersible in a liquid whose density is to be measured. This system is particularly suited to measuring the density of liquid mixtures such as liquid natural gas, which is a non-polar organic material that follows the Clausious-Mosotti equation establishing the relationship between dielectric constant and density. The signals derived from the compacitance probe and temperature sensor are scaled and used to calculate density pursuant to the Clausious-Mosotti equation.

U.S. Pat. No. 4,417,472 discloses a liquid level sensor comprising four elongated L-shaped conductive capacitor elements arranged in a cruciform configuration. The four L-shaped conductive elements are sandwiched with a material of known dielectric constant to comprise one solid cross of the cruciform and to provide two open capacitor-forming spaces in the other cross of the cruciform that receive varying levels of fluid, thereby forming two capacitors of variable capacitance depending upon the level of the fluid in the spaces.

U.S. Pat. No. 4,429,272 discloses an apparatus for detecting the presence of water in fuel for an internal combustion engine by the change in dielectric constant of the fuel detected by two electrodes immersed in the fuel.

U.S. Pat. No. 4,468,611 discloses a four cavity fluid cell for use in a Wheatstone bridge configuration to equalize the effects of fluid characteristics, pressure and temperature in the measurement of the dielectric constant of a sampled fluid. U.S. Pat. No. 4,468,611 discloses a plurality of configurations forming four fluid capacitance-determining cells for connection into the Wheatstone bridge, including four L-shaped elongated conductive capacitive elements arranged in a cruciform configuration and supported by a central dielectric member and a surrounding dielectric member to form four capacity cells in the arms of the cruciform. One of the opposing pairs of open cells is provided with reference fluid and the other opposing pair of fluid cells is provided with sample fluid whose dielectric constant is to be determined.

U.S. Pat. No. 4,673,869 discloses a circuit for matching of the capacitance of the sample and reference cells from outside the oven of a chromatographic analyzer system. The circuit includes a dielectric constant detector including a detection cell providing a sample cell formed by a pair of cylindrical electrodes spaced apart along a common axis and surrounded by a common electrode. When the same fluid is going through both the sample and reference cell, a voltage applied to the varactor diode is manipulated until such time as the capacitance of the sample and reference cell are substantially matched.

U.S. Pat. No. 4,751,476 discloses a device and method for distinguishing between different fluids on the basis of their dielectric properties. The disclosed device includes two substantially parallel conductive surfaces that are positioned on opposite sides of a fluid conduit to form a substantially parallel plate capacitor. One of the conductive surfaces is connected through an inductor to a voltage source and the other of the conductive surfaces is connected to a resonator device. A transconductance amplifier is connected between the resonator device and the first conductive surface. The system provides oscillation when a known fluid passes between the parallel conductive plates but no oscillation when the fluid having different electrical dielectric properties passes between the plates because of the change of the capacitance due to differing dielectric constants.

Notwithstanding this prior inventive activity, a satisfactory density sensor for cryogens such as slush hydrogen and the like remained unavailable prior to this invention.

DISCLOSURE OF THE INVENTION

This invention provides a light-weight density sensor having a rigid open structure that does not impede fluid flow and further provides the ability to accurately and reproducably measure dielectric constants and densities over long distances without interference from connecting coaxial cables during periods of vibration and thermal shock.

The invention comprises a novel immersion cell and an oscillator circuit that provide a variable frequency output related to the dielectric constant of the cryogen within the immersion cell and from which the density of the cryogen can be determined. The immersion cell comprises an elongated conductor located centrally within a space formed by a plurality of outer elongated conductors spaced around the central conductor. The plurality of outer elongated conductors are electrically interconnected to form an open outer electrode. The open outer electrode does not impede the flow of cryogen into the immersion cell and by its structure permits accurate density determinations dependent upon the dielectric constant of cryogen present within the cell.

In a preferred embodiment of the apparatus, the immersion cell is carried by a circuit housing for the oscillator formed of an electrically conductive material. The central electrode and the plurality of conductors forming the open outer electrode are carried at one end by the circuit housing. A wall of the circuit housing mechanically and electrically interconnects the plurality of outer conductors and further carries a dielectric support that carries the inner conductor and electrically isolates it from the plurality of outer conductors. The inner conductor and plurality of outer conductors are held at their other ends by a support of electrically non-conductive material to provide a rigid and economical structure. The oscillator circuit within the preferred environment is preferably the type commonly referred to as the Clapp LC Oscillator.

The immersion cell sensor of this invention is open to slush cryogens and its inner conductor is electrically shielded by the open outer electrode formed by the plurality of the elongated conductors.

In a preferred embodiment of this invention, the central electrode is a cylinder with a radius a, and the plurality of elongated outer conductors forming the open outer electrode comprise four cylindrical conductors equally spaced about the central cylindrical electrode on a circle having a radius b from the central axis of the central electrode, with their outer cylindrical surfaces having a radius b/4. With this preferred arrangement of the immersion cell, the capacitance may be determined from the formula $$C = \frac{2\pi\epsilon L}{Ln(b/a)},$$

where $\epsilon$ equals the dielectric constant of the cryogen and L equals the length of the immersion cell. The capacitance is insensitive to vibration and other displacements of the inner electrode and thermal contraction effects only the length term L with such an arrangement.

Further features of the invention will be apparent from the drawings and further description that follows.

BEST MODE FOR CARRYING OUT THE INVENTION

Figure 1:
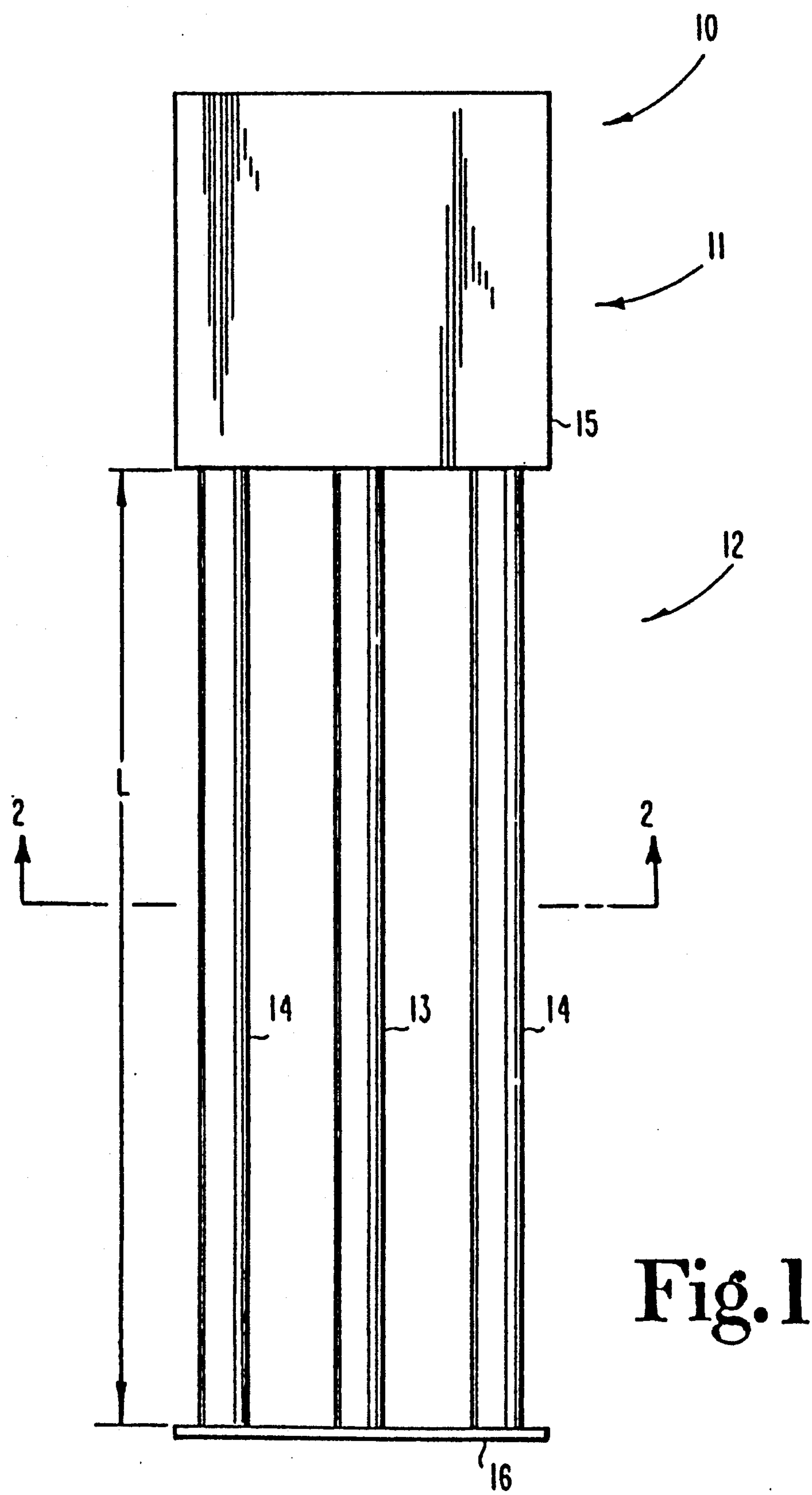
FIG. 1 is a plan view of a density sensor of this invention.
Figure 2:
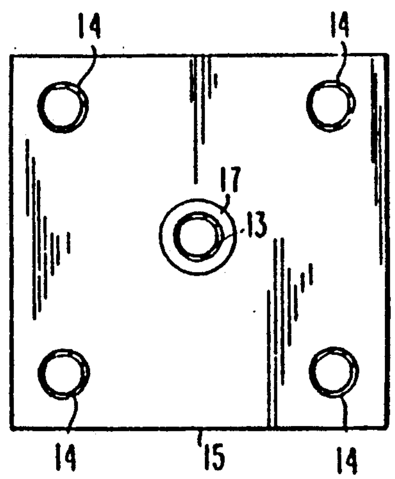
FIG. 2 is a cross-sectional view of the density sensor of FIG. 1 taken at plane 2—2 as shown on FIG. 1 through the immersion cell portion of the density sensor.

FIG. 1 shows a density sensor 10 of the invention. The density sensor 10 comprises a first portion 11 and a second portion 12. The second portion 12 comprises an immersion cell comprising an inner electrode in the form of an elongated central conductor 13 and an outer electrode in the form of a plurality of elongated outer conductors 14. The elongated central conductor 13 and plurality of the elongated outer conductors 14 are carried at their one ends by a housing 15 of the first portion 11 and are supported at their distal ends by a support 16 of electrically non-conductive material. Preferably, the housing 15 is formed from electrically conductive metal, such as copper, stainless steel, etc., to form a circuit compartment and to provide electromagnetic shielding for the circuit of the density sensor. As shown in FIG. 2, the plurality of outer electrodes 14 are electrically and mechanically connected to the housing 15 to form the outer electrode. The electrical- mechanical connection of the outer conductor can be made by any convenient fastening method known in the art, such as by soldering, brazing, welding or by threaded fasteners and the like. The outer electrode of the immersion cell may be formed by integral extensions of housing 15. The inner elongated conductor 13, as shown in FIG. 2, is supported in spaced relationship from the walls of housing 15 by an electrically non-conductive support 17. The electrically isolating supports 16 and 17 may be any structurally sound, electrically non-conductive material such as nylon, polypropylene or any like reinforced insulating material. Elongated conductor 13 may thus be used as an electrode centrally located within an outer electrode 14 formed by the plurality of elongated conductors 14. The density sensor is thus a rigid, lightweight, one-piece structure adapted for convenient use over a wide temperature range from cryogenic temperatures to temperatures of 1000° F. and higher.

Figure 3:
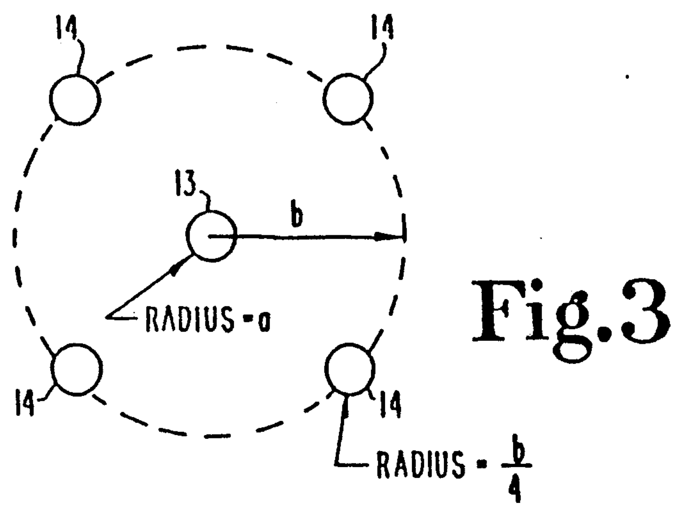
FIG. 3 is a diagramatic representation of a preferred immersion cell arrangement of this invention.

A preferable arrangement for the plurality of conductors 14 forming the outer electrode and the elongated conductor 13 forming the inner electrode is shown diagramatically in FIG. 3. The number of conductors 14 and their diameters are preferably chosen to provide effective shielding of the inner electrode. Where the outer electrodes are equally spaced about the inner electrode at a distance b, their outer diameters are preferably equal to b/n, where n equals the number of outer conductors 14. It is preferable that the outer electrode be comprised of four elongated tubular conductors, as shown in FIGS. 1-3, equally spaced on a circle having a radius b from the central axis of the inner conductor 13, which is itself preferably an elongated tubular conductor. As indicated in FIG. 3, the preferred radius of the cylindrical outer surface of the plurality of elongated tubular conductors making up the outer electrode is equal to the radius b divided by 4, the number of rods. If the radius of the cylindrical outer surface of the inner elongated tubular conductor is a, then the capacitance between the inner electrode 13 and the plurality of conductors 14 is defined by the following relationship:

$$C = \frac{2\pi\epsilon L}{Ln(b/a)},$$

where =the dielectric constant of the material between the inner and outer electrodes 13 and 14, and L=the length of the inner and outer electrodes 13 and 14 of the immersion cell 12, as shown in FIG. 1.

Thus the inner conductor 13 of plurality of outer conductors 14 form a capacitor open to slush flow. The inner conductor 13 is electrically shielded by the plurality of outer conductors 14 forming the outer electrode so the capacitance between the inner electrode 13 and outer electrodes 14 is independent of the presence of nearby conductors and permits the immersion cell 12 to approach and be located close to the walls containing a fluid without interfering with the density measurement when the immersion cell is immersed in a cryogen or other fluid. The capacitance of the open cage capacitor formed by immersion cell 12 is insensitive to the displacement of the inner rod, and thermal contraction effects only the length of the cell L, which is predictable.

Figure 4:
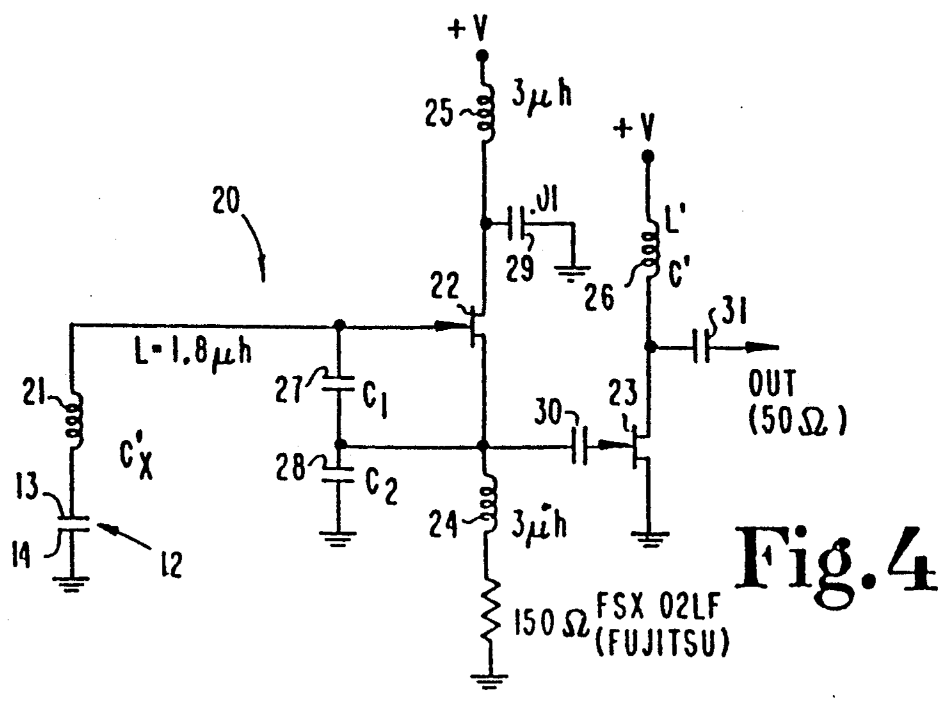
FIG. 4 is a circuit diagram of a preferred density sensing circuit of this invention.

As shown in FIG. 4, a preferable circuit for use with the immersion cell 12 is a Clapp LC Oscillator 20. FIG. 4 is a circuit diagram of a preferred oscillator, which in this invention is preferably enclosed within the electronics compartment formed by the walls of housing 15. As shown in FIG. 4, the immersion cell 12 forms a capacitor in the oscillator circuit with the outer electrode formed by the plurality of conductors 14 connected with the ground and the inner electrode 13 connected with an inductor 21. The capacitance of the immersion cell 12 can be small, for example, about 6pF, and as shown below, all other capacitors add in series so that the overall capacitance across inductor 21 is essentially that of the immersion cell 12. As shown in FIG. 4 semiconductor devices 22 and 23, conductors 24, 25 and 26 and capacitors 27, 28, 29, 30 and 31 form, in conjunction with inductor 21 and immersion cell 12, an oscillator whose frequency varies with the capacitance between the inner conductor 13 and plurality of outer conductors 14 comprising the outer electrode. GaAs field effect transistors (FETs), e.g., FSX02LF (FUJITSU), are preferably used as semiconductor devices 22 and 23, and the LC oscillator can be immersed in slush hydrogen, thereby providing a constant temperature environment and avoiding microphonic-sensitive interconnecting leads.

The dielectric constant $\epsilon$ of a material in the space between the inner electrode 13 and plurality of outer conductors 14 may be determined as follows:

$$f = \frac{1}{2\pi\sqrt{LC}};$$

$$\frac{1}{C} = \frac{1}{C'_x} + \frac{1}{C'_1} + \frac{1}{C'_2},$$

where $C'_x$=the capacitance between inner electrode 13 and the outer electrode formed by a plurality of conductors 14, $$C'_x = \epsilon C_x = \frac{2\pi L\epsilon}{ln(b/a)};$$

$C'_1=C_1+C_{out}$ and $C'_2=C_2+C_{in}$ and where $$\frac{1}{\epsilon} = af^2 + b = (4\pi^2 L\, C_x)f^2 - \left(\frac{C_x}{C_1 + C_{out}} + \frac{C_x}{C_2 + C_{in}}\right),$$

and $C_{out}$, $C_{in}$=output and input capacitance of FET, 22.

Thus the density sensor 10 of the invention determines the density of any cryogenic liquid, solid or gas between the inner electrode 13 and outer electrode formed by conductors 14, which form an open cage capacitor. The invention provides direct conversion of dielectric constant information to a frequency signal of the site of measurement, and with proper buffering, the frequency signal can be carried around an aircraft without vibrations, temperature changes and other environmental changes affecting significantly signal accuracy. The density sensor of the invention permits the measurement of slush hydrogen and allows an accurate measurement of the mass of hydrogen loaded onto a plane with the minimum added system weight.

The density sensor of the invention can be made, for example, with a weight of no more than 165 grams (0.36 pounds). In a preferred embodiment of density sensor, the inner and outer conductors can be aluminum tubes having a diameter of $\frac{3}{8}$ to $\frac{1}{2}$ inch and a length of about 6 to 7 inches, but the inner and outer electrodes can be configured to meet the space requirements of different applications. The density sensor will consume minimal power of one volt at about 10 milliamps and provide accurate outputs at long distances without interference from the characteristics of interconnecting coaxial cables, vibration or thermal shocks. The preferred density sensor is a rigid structure of lightweight, and is capable of many thermal cycles and has demonstrated accuracies better than $\pm 0.5\%$ for slush hydrogen between 0–30% v/v.

While the preceding description illustrates the presently known best mode for carrying out the invention, the scope of the invention is not limited, as will be apparent to those skilled in the art, to the described best mode and is limited only by the scope of the invention, the following claims and the prior art.

We claim:

1. An apparatus for measuring the density of cryogens, comprising an immersion cell comprising an elongated inner conductor and four elongated outer conductors equally spaced about the elongated inner conductor, said four outer conductors being electrically connected together and supported at a fixed distance about said inner conductor, said inner conductor being electrically isolated from said four outer conductors and supported centrally within said four outer conductors by an electrically isolating support; and an oscillator connected with said inner conductor and with said four outer conductors, said oscillator providing a varied frequency output dependent upon the density of a cryogen that may be disposed between said elongated inner conductor and said four elongated outer conductors.

2. The apparatus of claim 1 wherein each of said four elongated outer conductors comprises a conductive metallic surface in the form of a right circular cylinder.

3. The apparatus of claim 2 wherein said elongated central conductor comprises a conductive metallic surface in the form of a right circular cylinder.

4. The apparatus of claim 3 wherein the central axes of said elongated central conductor and said four elongated outer conductors are parallel.

5. The apparatus of claim 4 wherein said elongated central conductor and outer conductors are metal tubes.

6. The apparatus of claim 2 wherein the four elongated right circular cylindrical outer conductors are located equidistantly at a radius b from the central axis of the central elongated conductor and each have a radius b/4.

7. The apparatus of claim 1 wherein said oscillator includes one or more gallium arsenide field effect transistors.

8. An apparatus to determine the density of a cryogen, comprising an immersion cell carried by a housed oscillator and operable to provide a variable frequency output from said oscillator related to the density of a cryogen within the immersion cell, said immersion cell comprising an elongated electrode located centrally within and spaced from a plurality of outer elongated conductors, said plurality of outer elongated conductors being equally spaced around said central conductor and electrically interconnected to form an open outer electrode, said central electrode and open outer electrode being supported and carried by said housed oscillator at their one ends and by a support at their other ends to form a known electrical capacitance in the absence of cryogen and a varying capacitance dependent upon the density of a cryogen present between the central electrode and the open outer electrode, said central electrode and open outer electrode being connected with said oscillator to provide a variable frequency oscillator output from which the density of the cryogen can be determined.

9. The apparatus of claim 8 wherein the central electrode and the plurality of outer elongated conductors have outer surfaces in the form of right circular cylinders, and the plurality of outer elongated electrodes are located equidistantly at a radius b from the central axis of the central electrode, and each of the outer surfaces of each of the outer elongated electrodes has a radius b/n, where n is the number of outer elongated electrodes.

10. The apparatus of claim 8 wherein each of said plurality of outer elongated conductors comprises a conductive metallic surface in the form of a right circular cylinder.

11. The apparatus of claim 10 wherein said elongated central conductor comprises a conductive metallic surface in the form of a right circular cylinder.

12. The apparatus of claim 11 wherein said plurality of outer elongated conductors comprises four electrodes in the form of right circular cylinders, and the central axes of said elongated central conductor and said four elongated outer conductors are parallel.

13. The apparatus of claim 12 wherein said elongated central conductor and outer conductors are metal rods.

14. The apparatus of claim 12 wherein the four elongated right circular cylindrical outer conductors are located equidistantly at a radius b from the central axis of the central elongated conductor and each elongated outer electrode has a radius of b/4.

15. The apparatus of claim 8 wherein said oscillator is carried within a conductive container having an end carrying said central conductor and said plurality of outer elongated conductors, each of said outer elongated conductors being mechanically and electrically connected to said conductive container end, and wherein an insulator is carried by the end of said conductive container and said insulator supports said central conductor and electrically isolates said central conductor from said conductive container.

16. The apparatus of claim 8 wherein said oscillator comprises an inductor having a known inductance connected with said central conductor at one end and connected with the remainder of the oscillator circuit at the other end, the inductance of said inductor and the capacitance between said central conductor and said plurality of outer elongated conductors determining the frequency of said oscillator.

17. The apparatus of claim 16 wherein said oscillator is a Clapp LC oscillator including one or more gallium arsenide field effect transistors.

18. An immersion cell, comprising an elongated electrode located centrally within and spaced from a plurality of outer elongated conductors spaced around said central electrode, said spaced outer elongated conductors being electrically interconnected to form an open outer electrode, and an oscillator connected with said central electrode and said open outer electrode, said oscillator being housed by a rigid container having a wall carrying said central electrode and said open outer electrode at their one ends, their other ends being carried by a rigid supporting structure, said wall and said supporting structure electrically isolating said central electrode from said open outer electrode so that upon immersion of the immersion cell into a cryogen, the density of the cryogen can determine the frequency of the oscillator.

19. An apparatus for measuring the density of cryogens, comprising an immersion cell comprising an elongated central cylindrical conductor and four elongated outer cylindrical conductors equally spaced about the elongated central conductor, said four elongated outer cylindrical conductors each having a radius b/4 and being electrically connected together and supported on a circle having a radius b from the central axis of said central cylindrical conductor, said elongated central cylindrical conductor having a radius a and being electrically isolated from said four elongated outer cylindrical conductors; and an oscillator connected with said elongated central cylindrical conductor and with said four elongated outer cylindrical conductors, said oscillator being adapted to provide a varied frequency output dependent upon the density of a cryogen that may be present between said elongated central cylindrical conductor and said four elongated outer cylindrical conductors and being determined by the relationship $$\frac{1}{\epsilon} = af^2 + b.$$

* * * * *